(12) United States Patent
Saito

(10) Patent No.: US 6,824,824 B2
(45) Date of Patent: Nov. 30, 2004

(54) METHOD FOR RECYCLING ORGANOMETALLIC COMPOUND FOR MOCVD

(75) Inventor: Masayuki Saito, Kanagawa (JP)

(73) Assignee: Tanaka Kikinzoku Kogyo, K.K., Tokyo (JP)

( * ) Notice: Subject to any disclaimer, the term of this patent is extended or adjusted under 35 U.S.C. 154(b) by 0 days.

(21) Appl. No.: 10/394,003

(22) Filed: Mar. 24, 2003

(65) Prior Publication Data

US 2003/0180463 A1 Sep. 25, 2003

Related U.S. Application Data

(62) Division of application No. 09/824,234, filed on Apr. 3, 2001, now Pat. No. 6,610,873.

(30) Foreign Application Priority Data

Aug. 3, 2000 (JP) ........................................ 2000-235092

(51) Int. Cl.[7] .......................... C23C 16/00; C07F 15/00
(52) U.S. Cl. .............................. 427/255.28; 427/248.1; 427/593; 556/1; 556/43; 556/52; 556/53; 556/58; 556/110
(58) Field of Search .......................... 427/255.28, 248.1, 427/593; 556/1, 43, 52, 53, 58, 110

(56) References Cited

U.S. PATENT DOCUMENTS

| | | | | |
|---|---|---|---|---|
| 6,002,036 A | * | 12/1999 | Kadokura | .................... 556/136 |
| 6,420,582 B1 | * | 7/2002 | Okamoto | .................... 556/136 |
| 6,465,669 B1 | * | 10/2002 | Okamoto | .................... 556/136 |
| 6,476,247 B1 | * | 11/2002 | Okamoto et al. | ........... 556/136 |

FOREIGN PATENT DOCUMENTS

JP          2002053961 A   *  2/2002   ........... C23C/16/44

* cited by examiner

Primary Examiner—Porfirio Nazario-Gonzalez
(74) Attorney, Agent, or Firm—Rothwell, FIgg, Ernst & Manbeck, P.C.

(57) ABSTRACT

The present invention is a method for recycling an organometallic compound for MOCVD comprising extracting an unreacted organometallic compound from a used raw material which has undergone a thin film production process, wherein the unreacted organometallic compound is extracted after the used raw material is subjected to a reforming treatment. The method for reforming the used raw material is either a method for contacting the used raw material with a hydrogenation catalyst or a reducing agent or a method for contacting the used raw material with either a halogen, a hydrogen halide, an inorganic acid, an alkene, or a diene. In this case, an organometallic compound of higher purity can be obtained through this recycling method by contacting the used raw material with a decoloring agent comprising activated carbon, silica, or activated clay.

72 Claims, 3 Drawing Sheets

Retention Time

Retension Time

METHOD FOR RECYCLING ORGANOMETALLIC COMPOUND FOR MOCVD

CROSS-REFERENCE TO RELATED APPLICATIONS

This is a divisional application of application Ser. No. 09/824,234, filed Apr. 3, 2001, now U.S. Pat. No. 6,610,873 B2.

BACKGROUND OF INVENTION

1. Field of the Invention

The present invention relates to a method for purifying an organometallic compound in a reusable state from an exhaust gas after thin film formation in the CVD method using an organometallic compound as a raw material.

2. Description of the Related Art

Since the chemical vapor deposition method (hereinafter referred to as CVD method) has the advantages that it can easily prepare uniform thin films and it is superior in step coverage, the method is one of the thin film-forming technologies generally employed for production of film electrodes in semiconductor devices. The CVD method is considered to become a major process for preparation of film electrodes in the future because the method can provide further densification required of recent circuits and electronic parts.

The CVD method is a preparation method of a thin film of a metal or a metal oxide, which involves vaporizing a raw metal compound to transport the same to the surface of a substrate, reacting the transported raw material particle on the substrate to accumulate as a metal or a metal oxide to form a thin film. As a raw material of metal compound, in particular, organometallic compounds, which have low melting points and are easy to handle, are used (the CVD method using an organometallic compound is hereinafter referred to as MOCVD).

Incidentally, the production costs of thin films by the MOCVD method depend on the prices of organometallic compounds which are raw materials and the ratio of the amount of the organometallic compounds consumed in the reaction to the amount of the compound introduced on the surface of a substrate, i.e., the utilization ratio, and the utilization ratio in the conventional MOCVD method is 10% or lower, which means most of the introduced source gas is actually disposed as an exhaust gas. Therefore, the production costs of thin films with such low utilization ratios are strongly influenced by the prices of organometallic compounds.

In this connection, the prices of organometallic compounds are generally high because their synthesis require multiple steps. For example, copper itself is not expensive as a metal but the price significantly increases when an organometallic compound thereof is synthesized. Therefore, it is considered that the high costs of forming thin films according to the conventional MOCVD method with low utilization ratios cannot be avoided due to the high prices of organometallic compounds.

Specifically, thin films of precious metals such as ruthenium and iridium are being employed recently for higher performance of film electrodes and since precious metals are trace metals and are expensive themselves, organometallic compounds thereof are significantly expensive. Therefore, the production costs of thin films of precious metals according to the conventional MOCVD method are expected to be extremely high.

As described earlier, the organometallic compounds are easy to handle and capable of forming thin films efficiently and they are expected to be increasingly employed. Therefore, if demand for the organometallic compounds increases, the conventional MOCVD method with low utilization ratios has the disadvantages relating to the production costs of thin films and about deletion of resources due to a huge lose of the materials.

The applicant developed a recycling method of organometallic compounds for MOCVD wherein an unreacted organometallic compound component is extracted from a used raw material which was conventionally discarded and then purified to a reusable state, as a method for reducing the production costs of thin films and avoiding depletion of resources, and filed a patent application for an MOCVD thin film production process incorporating this recycling technology (application No. 2000-96359). This recycling technology involves purification and extraction of organometallic compounds by passing the raw material after the thin film formation, for example, through a cold trap to cool and condense to recover the same in a liquid state and distilling the recovered material under appropriate conditions. This technology can avoid wasting organometallic compounds and hence reduce the production costs of thin films.

Although the main point of the above-mentioned MOCVD thin film production process resides in the recycling technology, the recycling technology needs some improvements. The recycled organometallic compounds should have substantially as high purity as the virgin material in order to produce thin films with comparable properties to those made from the virgin material. It is also required that as much organometallic compounds as possible be extracted from a used raw material in order to reduce the production costs of thin films. In particular, the purity is extremely important for organometallic compounds for use as a raw material for MOCVD and if an organometallic compound containing a trace amount of impurities is used as a raw material for MOCVD, the purity of the thin film also decreases, which may affect the electric characteristics and influence the morphology of the film.

The present invention has been made under these situations and proposes an improved recycling method of organometallic compounds in which an unreacted organometallic compound is extracted from a used raw material which has undergone the CVD steps and recycled, wherein the organometallic compound of high purity is extracted efficiently.

SUMMARY OF THE INVENTION

The inventor has examined improvements in order to improve the above-mentioned recycling technology. As a result, the inventor has conceived the idea that it is necessary to assess the possibility that reaction products formed by the thin film formation reaction and its side reaction are present in a used raw material, and their properties and effects in order to complete a superior recycling technology.

In view of the effects of reaction products here, if the reaction products can be removed by normal reparation methods such as distillation, they do not signify aside from a reduction in the yield. In this connection, the inventor has thought the reaction products already identified in the conventional researches do not matter. The reason is that the impurities identified in these conventional researches include low molecular weight compounds such as water, carbon dioxide, aldehydes, and formic acid, which are originated from decomposed organometallic compounds due to leaving of metal atoms and these low molecular weight compounds have significantly different properties from those of the organometallic compounds from which they are to be separated and thus can be easily separated by normal separation methods such as distillation. Therefore, it is considered if the actual CVD thin film formation process produces only these compounds, the above-mentioned conventional recycling technology can sufficiently cope with the compounds.

However, the inventor has examined a used raw material after the thin film formation reaction in detail, and found that the actual CVD thin film formation process produces the above-mentioned low molecular weight compounds as reaction products, but also produces other reaction products due to unreported side reactions.

In this connection, a case is taken as an example for illustration in which a ruthenium thin film is produced with diethylruthenocene represented by Formula 1, which is recently receiving attention as a raw material for ruthenium thin films, and its used raw material is recycled.

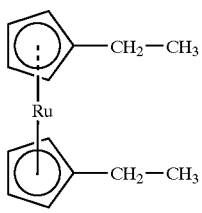

Formula 1

Diethylruthenocene, represented by Formula 1, is a compound composed of a ruthenium atom as a metal atom and two ethyl derivatives of cyclopentadiene coordinating to the metal as ligands. The CVD thin film formation process with diethylruthenocene involves a decomposition reaction of diethylruthenocene on a substrate to accumulate ruthenium.

The inventor has fully examined the composition of the used raw material after the thin film formation with diethylruthenocene and found the used raw material contains predominantly unreacted diethylruthenocene but the following two kinds of side reaction products are also present.

The first kind of side reaction products include, for example, organic ruthenium compounds (the following formula) with an alcohol group, a carbonyl group, an ether group, and the like to which the ethyl group (a substituent of the ligand) on the cyclopentadiene ring is oxidized. It is considered that these compounds are formed by reactions between unreacted diethylruthenocene which has not been involved in the thin film formation reaction and oxygen, which is generally added as a reactant gas when thin films are formed by using relatively stable organometallic compounds such as diethylruthenocene.

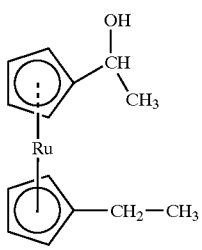

Formula 2

The second kind of side reaction product is vinylcyclopentadienyl(ethylcyclopentadienyl)ruthenium represented by the following formula formed by another side reaction in the thin film formation reaction in which unreacted diethylruthenocene is dehydrogenated. An ethyl group of diethylruthenocene is dehydrogenated into a vinyl group to form vinylcyclopentadienyl(ethylcyclopentadienyl) ruthenium. Although the factors responsible for the dehydrogenation reaction are not clear, the inventor believes that the dehydrogenation reaction occurs by the catalytic action of ruthenium atom leaving from diethylruthenocene due to decomposition of the thin film formation. It is thought the dehydrogenation reaction is more likely to occur especially in the thin film formation with organometallic compounds having functional group on the ligands coordinating to metal atoms.

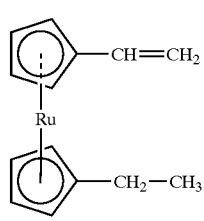

Formula 3

It is thought the thin film formation and side reactions attributable to the organometallic compounds decomposed in the film formation reaction as well as oxidation reactions and dehydrogenation reactions toward the unreacted organometallic compounds occur in the thin film formation process in the actual MOCVD method as in the case of diethylruthenocene. Therefore, the inventor has examined a possibility for removal of oxides and dehydrogenated products of these unreacted organometallic compounds and its approach. As a result, the inventor has conceived the understanding the products generated by the oxidation reaction can be removed by normal separation methods such as distillation, but the reaction products formed by the dehydrogenation reaction have similar properties such as molecular weights and boiling points to those of the organometallic compounds to be extracted, and it is impossible to separate those components by normal separation methods such as distillation. The inventor has reached the conclusion that if the problem about these irremovable dehydrogenated products is left unsolved, the yield of recycled organometallic compounds and the purity decrease and, therefore, the electric characteristics and morphology of the thin film produced therefrom also deteriorate.

Consequently, the inventor has intensively investigated to search for methods for removing these dehydrogenated products and found the following two approaches to the removal.

The first method for removing the hydrogenated products is a reforming treatment in which the reaction products are hydrogenated or reduced to the original organometallic compounds followed by purification of the organometallic compounds.

Accordingly, the first invention of the present application is a recycling method of the organometallic compounds for MOCVD in which unreacted organometallic compounds are extracted from a used raw material which has undergone the thin film formation process, wherein the unreacted organometallic compounds are extracted after the used raw material is reformed by contacting the same with a hydrogenation catalyst or a reducing agent.

The first method converts the dehydrogenated products, which are contained in the used raw material and are difficult to separate, into the original organometallic compounds. Therefore, according to the present invention, the dehydrogenated products which are impurities disappear due to the reforming treatment, which improves the purity of the organometallic compounds to be purified later. The organometallic compounds thus obtained can be used as a raw material for MOCVD again. Because the first method converts the dehydrogenated products which are impurities into the original organometallic compounds, the concentration of the original organometallic compounds in the used raw material also increases. This also improves the yield of the organometallic compounds in the purification.

Although those generally known as hydrogenation catalysts or reducing agents can be used as the hydrogenation catalysts or reducing agents employed in the method here, either platinum catalyst, palladium catalyst, ruthenium catalyst, or Raney nickel catalyst is preferably used as the hydrogenation catalyst. As the reducing agent, sodium borohydride ($NaBH_4$), lithium aluminium hydride ($LiAlH_4$) calcium hydride ($CaH_2$), dimethylaminoborane ($C_2H_7NBH_4$), trimethylaminoborane ($C_3H_9NBH_4$), or hydrazine ($NH_2NH_2$) is preferably used.

The second method for removing the dehydrogenated products of the organometallic compounds is a method in which the organometallic compounds are purified after the dehydrogenated products are subjected to a reforming treatment to convert the same to other compounds removable by separation methods such as distillation. The method for converting the dehydrogenated products to other compounds removable by separation methods such as distillation include addition reactions of halogen or hydrogen halide, addition reactions of water, addition reactions of alkenes, and addition reactions of dienes (Diels-Alder reaction) toward the dehydrogenated products.

The second invention of the present application is a recycling method of the organometallic compounds for MOCVD in which unreacted organometallic compounds are extracted from a used raw material which has undergone the thin film formation process, wherein the unreacted organometallic compounds are extracted after the used raw material is subjected to a reforming treatment by contacting the same with either a halogen, a hydrogen halide, an inorganic acid, an alkene, or a diene.

According to the second method, the dehydrogenated products of the organometallic compounds, which are contained in the used raw material and are difficult to separate, are subjected to halogen addition or hydration to change to other compounds having increased molecular weights or different boiling points. As a result, it is possible to remove the converted dehydrogenated products in the subsequent purification process of the organometallic compounds. Therefore, the second method can purify the organometallic compounds of high purity, which can be used as a raw material for MOCVD again.

Incidentally, the compounds for the reforming treatment of the used raw material include halogens such as chlorine, bromine, and iodine, hydrogen halide such as hydrogen chloride, hydrogen bromide, and hydrogen iodide, and inorganic acids such as hydrochloric acid and sulfuric acid. The alkene includes maleic anhydride and the diene includes 2-methyl-1,3-butadiene.

The recycling method according to the present invention can prevent the dehydrogenated products of the unreacted organometallic compounds, which are impossible to separate and remove, from remaining in the organometallic compounds to be recycled and allows the organometallic compounds of high purity to be recycled.

According to the inventor, it is more preferable the unused organometallic compounds are extracted after the used raw material is subjected to a decoloring treatment by contacting the same with a decoloring agent comprising either activated carbon, silica, or activated clay in order for the organometallic compounds of high purity to be recycled.

The decoloring treatment is set in view of the fact that the raw material for MOCVD may undergo a phenomenon in which it colors through the thin film formation process as in the case, for example, where diethylruthenocene, which is originally pale yellow, turns brown through the thin film formation process. The reason for the coloring is not clear but, according to the inventor, there is a problem that the used raw material thus colored is purified by a normal purification method to obtain the organometallic compounds having the same color and the decoloring treatment is to solve this problem. As the decoloring agent for decoloring, activated clay is employed in the present invention. This selection is made based on the finding that activated carbon is effective for decoloring the used raw material for MOCVD to which the present invention is directed by the trials by the inventor although it is known that activated carbon, silica, and activated clay generally adsorb a variety of materials and have deodorizing and decoloring effects.

Incidentally, the decoloring treatment may be conducted either before or after the above-mentioned reforming treatment. The decoloring treatment may be omitted when a precious metal catalyst such as platinum catalyst, palladium catalyst, or ruthenium catalyst is employed as a hydrogenation catalyst in the above-mentioned first recycling method. These precious metal catalysts generally have activated carbon as a support, which naturally functions as a support and also as a decoloring agent and therefore the reforming and decoloring treatments are simultaneously conducted when the precious metal catalyst is employed. However, a platinum catalyst and the like are used both as a decoloring agent and a reforming agent, the life of the hydrogenation activity may be shortened due to adherence of poisons attributed to coloring components to the catalyst. Therefore, when this situation is anticipated, it may be decided in view of the economy of the process whether the decoloring and reforming treatments are simultaneously conducted by a hydrogenation catalyst or the decoloring treatment by activated carbon and the reforming treatment by a hydrogenation catalyst are conducted separately.

Incidentally, the present invention is characterized in that the used raw material which has undergone the thin film formation process is subjected to the reforming treatment and/or the decoloring treatment before purification of the organometallic compounds. Therefore, there are no specific limitations to methods for recovering the used raw material before these treatments and methods for extracting and purifying the organometallic compounds from the used raw material after these treatments.

However, a step to remove oxygen from the used raw material which has undergone the thin film formation process is preferably included before the reforming treatment and/or the decoloring treatment in order to improve the yield of the organometallic compounds to be recycled. As mentioned above, oxygen may be added as a reactant gas in the MOCVD method and the oxydation reaction of the unreacted organometallic compounds may occur in the thin film formation reaction as mentioned above as well as in the recovering step when the organometallic compounds are recovered in the presence of oxygen, leading to a decrease in the yield. The methods for removing oxygen from the used raw material include contacting the used raw material with a deoxidizing agent such as silicagel.

As for the method for recovering the used raw material, the used raw material is preferably cooled to a liquid in view of easy handling in the subsequent steps, which is subsequently subjected to the reforming treatment and/or the decoloring treatment. Although the cooling conditions depend on the properties of the organometallic compounds, non-subliming organometallic compounds are preferably cooled to a temperature 30° C. lower than the boiling points and subliming organometallic compounds are preferably cooled to a temperature 30° C. lower than the melting points in order to fully liquefy the used raw material emitted in gaseous form. Specific approaches to the method include, for example, a method in which a cold trap is placed downstream from the reaction chamber and the used raw material is cooled in the cold trap to recover.

Furthermore, as the purification method of the organometallic compounds after the reforming treatment and the decoloring treatment, the organometallic compounds are preferably separated by distillation from the liquefied used raw material. Since the organometallic compounds have generally low melting points and low boiling points and undergo phase change at relatively low temperatures, it is possible to directly separate the organometallic compounds to high purity by distillation. Another reason is that distillation does not require a complicated apparatus and is a relatively easy purification method.

Incidentally, another preferable form as the method for purifying the organometallic compounds after the reforming treatment and the decoloring treatment is a method in which the used raw material after the reforming treatment and/or the decoloring treatment is subjected to column chromatography. This method enables separation and purification of highly pure organometallic compounds with an appropriate column packing. Moreover, the purification method using column chromatography is applied to the liquefied used raw material but also effective for the used raw material in gaseous form. Therefore one of the advantages of using column chromatography as a purification method is that the used raw material in gaseous form which has undergone the thin film formation process is directly purified without liquefying the same in the recovering step. Incidentally, either silicagel, octadecylsilane, alumina, porous polymers, graphite carbon, or zeolite is preferably used as a column packing for column chromatography.

Lastly, there is no specific limitation to the organometallic compounds for use in the present invention. Therefore, organic compounds of a variety of metals such as copper, indium, tantalum, tungsten, molybdenum, titanium, rhenium, barium, and strontium, which are generally used as raw materials for thin films conventionally, can be applied to the recycling method of the present invention. The prices of these metals are low themselves but corresponding organometallic compounds are significantly high in price and the recycling method can reduce the costs of thin film formation of these metals or metal oxides.

Moreover, the present invention is especially useful for recycling organometallic compounds comprising precious metals such as silver, gold, platinum, palladium, ruthenium, rhodium, iridium, and osmium in view of a recent increase in demand for thin films of precious metals and high prices of organometallic compounds of precious metals.

EMBODIMENT OF THE INVENTION

EXAMPLE 1

In this example, diethylruthenocene (a pale yellow liquid) is used as an organometallic compound raw material to produce a ruthenium thin film by the CVD method and the used raw material generated in the film formation is recovered, from which diethylruthenocene is extracted, and the recycled diethylruthenocene is used to produce a ruthenocene thin film again to examine its feasibility.

Figure 1:
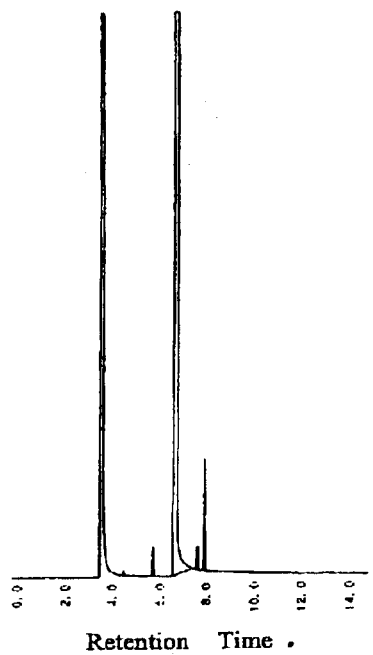
FIG. 1 is a gas chromatograph of diethylruthenocene used in Examples 1 and 2 and Comparative Example.

FIG. 1 shows a gas chromatograph of diethylruthenocene used as an initial raw material. FIG. 1 indicates that diethylruthenocene used in this example has a purity of 99.5% or higher.

Figure 2:
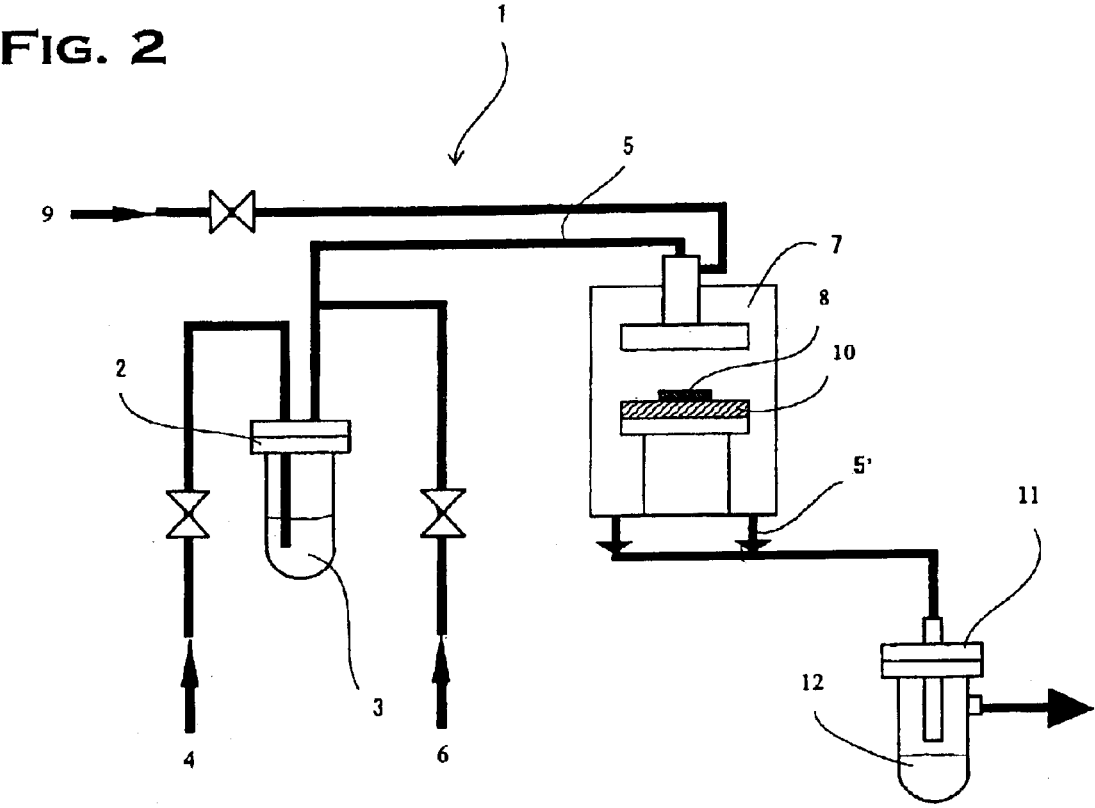
FIG. 2 is a schematic drawing of a CVD apparatus used in Examples 1 and 2 and Comparative Example.

FIG. 2 is a schematic drawing of the CVD apparatus 1 used in this example. In the CVD apparatus 1 in FIG. 2, diethylruthenocene 3 sealed in a thermostat, i.e. constant-temperature bath 2 is bubbled with argon gas 4 and heated to become a raw material gas 5, which is mixed with argon gas 6 as a carrier gas and transferred to the surface of the substrate 8 in the chamber 7. Furthermore, oxygen gas is introduced as a reactant gas for accelerating decomposition of diethylruthenocene into the chamber 7. Furthermore, oxygen gas 9 is introduced as a reactant gas in the chamber 7. Heating of the substrate 8 by the heater 10 effects the CVD thin film formation reaction on the substrate surface. A cold trap 11 to recover the used raw material in liquid form is placed downstream from the chamber, through which the raw material gas 5' after the reaction is passed to recover the liquefied used raw material 12.

An initial input of 100 g of diethylruthenocene was heated to 140° C. to vaporize for film formation. The thin film formation conditions are as follows:
Substrate temperature: 240° C.
Chamber pressure: approximately 665 Pa (5.0 torr)
Carrier gas flow: 200 sccm
Reactant gas flow: 200 sccm The cold trap 11 had a refrigerant flowing down its cooling surface and the raw material gas 5' which had undergone the reaction passing through the cold trap was cooled to approximately −10° C. The film formation was carried out till the raw material was completely consumed and 81.5 g of the used raw material 12 was recovered in the cold trap 11 as a used raw material (recovery rate, 81.5%). The used raw material had been brown.

The properties of the ruthenium thin film thus produced was examined to find a ruthenium purity of 98% and the morphology of the thin film was observed by an AFM (atomic force microscope) to find a surface roughness, $R_{ms}$, of 2.0 nm, which is an indication of a good thin film.

Figure 3:
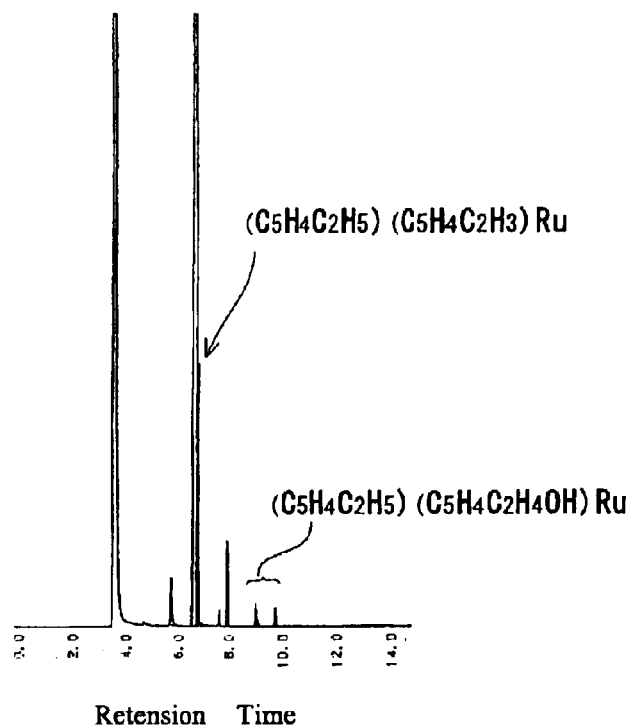
FIG. 3 is a gas chromatograph of the used raw material recovered in Example 1.
Figure 4:
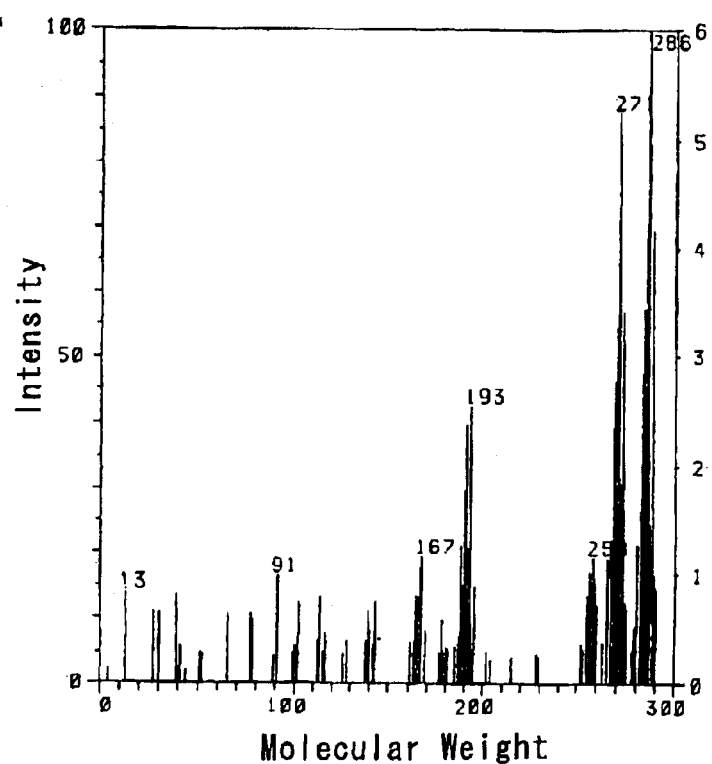
FIG. 4 is a profile of gas chromatography/mass spectroscopy of the used raw material recovered in Example 1.

On the other hand, the used raw material recovered was analyzed by gas chromatography to obtain a profile shown in FIG. 3. The gas chromatograph of the used raw material shows predominant peaks of diethylruthenocene and its purity of 98.37% as shown in FIG. 3 and a peak assignable to vinylcyclopentadienyl(ethylcyclopentadienyl)ruthenium was found overlapping these diethylruthenocene peaks. In order to confirm this assignment, the used raw material was analyzed by GCMS (gas chromatography/mass spectroscopy) to obtain a profile as shown in FIG. 4 to confirm this peak was assigned to vinylcyclopentadienyl (ethylcyclopentadienyl)ruthenium. Incidentally, the concentration of vinylcyclopentadienyl(ethylcyclopentadienyl) ruthenium is found to be 0.93% from the gas chromatograph in FIG. 3. Furthermore, the used raw material showed minor peaks assignable to various impurities which are considered to be formed due to oxidation of the ethyl group of diethylruthenocene as well as vinylcyclopentadienyl (ethylcyclopentadienyl)ruthenium as shown in FIG. 3.

Next, 0.5% palladium catalyst (support: activated carbon) was added to the used raw material to carry out hydrogenation to convert vinylcyclopentadienyl (ethylcyclopentadienyl)ruthenium to diethylruthenocene and to remove the colored components in the used raw material. The catalyst was then filtered out and the used raw material was subjected to reduced-pressure distillation at a temperature of 179° C. under a pressure of 17 Pa to purify diethylruthenocene. The concentration of diethylruthenocene thus purified was 99.6%, meaning a high purity. The weight of diethylruthenocene thus purified was 72.3 g and the yield with reference to the initial input is 72.3%.

Figure 5:
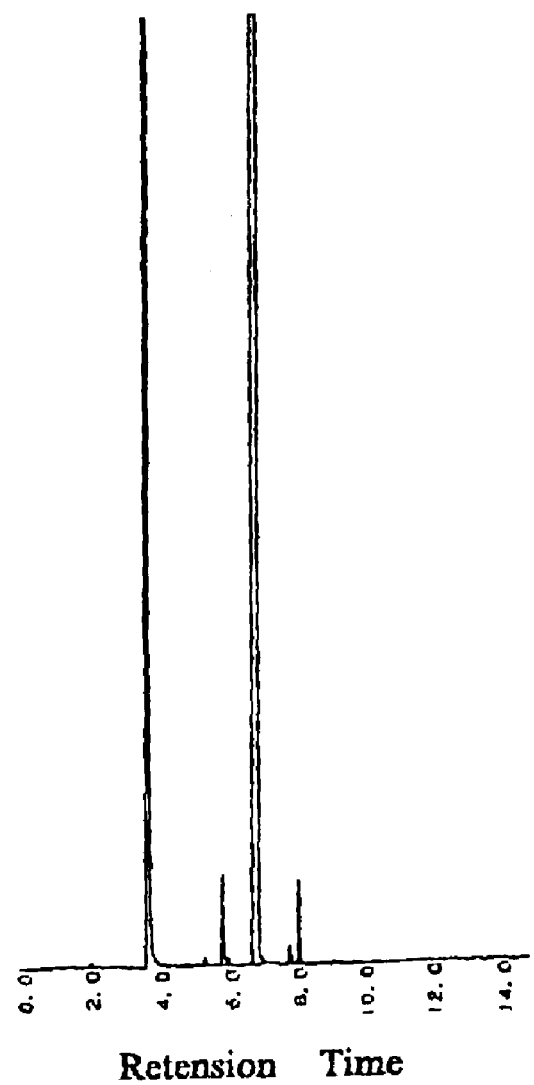
FIG. 5 is a profile of gas chromatography of diethylruthenocene purified in Example 1.

FIG. 5 shows a gas chromatograph of diethylruthenocene purified by the reduced-pressure distillation. The extract (diethylruthenocene) after the reduced-pressure distillation showed a similar form to diethylruthenocene which is an initial raw material and proved to be diethylruthenocene of high purity free from vinylcyclopentadienyl (ethylcyclopentadienyl)ruthenium and other impurities as shown in FIG. 5.

Diethylruthenocene purified in this way was used to produce a ruthenium thin film by the CVD method under the same conditions as above. As a result, the ruthenium film had a high purity of 98%, which was comparable to the purity of the film made from the initial raw material. The surface roughness of this thin film was measured to give an $R_{ms}$ of 2.0 nm, which showed a similar form to the thin film formed from the virgin raw material.

EXAMPLE 2

In this example, diethylruthenocene is used to produce a ruthenium thin film as an initial raw material as in Example 1 and the used raw material recovered in the process is reacted with bromine to convert vinylcyclopentadienyl (ethylcyclopentadienyl)ruthenium in the used raw material to ethylcyclopentadienyl(1,2-dibromoethylcyclopentadienyl)ruthenium represented by the following formula, which is removed to obtain highly purified diethylruthenocene.

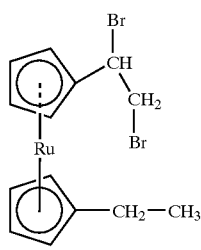

Formula 4

The same CVD apparatus and diethylruthenocene as in Example 1 were used in this example. The thin film production conditions and recovering conditions (the temperature at which the cold trap was cooled) were the same as in Example 1.

Then, 80.7 g of the recovered used raw material was dissolved in 500 ml of carbon tetrachloride ($CCl_4$) and 500 ml of a 0.1 mol/l bromine-carbon tetrachloride solution was added dropwise to this solution at room temperature and stirred for four hours. Subsequently, a 1 mol/l aqueous solution of sulfurous acid and a 1 mol/l aqueous solution of sodium hydroxide were added to the mixed solution to remove excess bromine.

The mixed solution thus treated was subjected to reduced-pressure distillation under the same conditions as Example 1.

Furthermore, diethylruthenocene purified in this Example was used to produce a ruthenium thin film by the CVD method as in Example 1 to prove to be capable of producing a good thin film excellent in purity and morphology. Comparative Example: A used raw material was subjected to reduced-pressure distillation without conducting the reforming treatment or the decoloring treatment by passing through the above-mentioned catalyst beforehand, to purify diethylruthenocene, as opposed to Examples 1 and 2. Diethylruthenocene thus purified was used to produce a ruthenium thin film by the CVD method and the ruthenium purity of the thin film was found to be 97%, which was a similar purity to the raw material recycled in Example 1, but the surface roughness, $R_{ms}$, was found to be 5.4 nm, which was extremely inferior in terms of the morphology.

From these results, it was confirmed diethylruthenocene purified from the used raw material in Examples 1 and 2 is capable of producing an extremely good thin film comparable to the film produced from a virgin raw material when reused as a raw material for MOCVD. On the contrary, diethylruthenocene purified directly from the used raw material shown in Comparative Example gave a thin film having imperfect properties, especially in terms of the morphology of the thin film. Although the difference between the morphologies shown in Examples and Comparative Example is of the order of nanometer and extremely small, such a slight difference exerts a significant influence in film electrodes for various semiconductor devices such as DRAMs, and the organometallic compounds recycled in Comparative Example cannot be used as a raw material for MOCVD for production of these thin film electrodes.

What is claimed is:

1. A method for producing a thin film by the CVD method with an organometallic compound purified by a method comprising extracting an unreacted organometallic compound from a used raw material which has undergone a thin film production process, wherein the unreacted organometallic compound is extracted after the used raw material is subjected to a reforming treatment by contacting the raw material with a hydrogenation catalyst or a reducing agent.

2. A method for producing a thin film as claimed in claim 1, wherein either platinum catalyst, palladium catalyst, ruthenium catalyst, or Raney nickel catalyst is used as a hydrogenation catalyst to reform the used raw material.

3. A method for producing a thin film as claimed in claim 1, wherein either sodium borohydride, lithium aluminium hydride, calcium hydride, dimethylamineborane, trimethylamineborane, or hydrazine is used as a reducing agent to reform the used raw material.

4. A method for producing a thin film by the CVD method wherein an organometallic compound is purified by the method, comprising extracting an unreacted organometallic compound from a used raw material which has undergone a thin film production process, wherein the unreacted organometallic compound is extracted after the used raw material is subjected to a reforming treatment by contacting the raw material with either halogens, hydrogen halides, inorganic acids, alkenes, or dienes.

5. A method for producing a thin film as claimed in claim 4, wherein either chlorine, bromine, or iodine is used as a halogen to reform the used raw material.

6. A method for producing a thin film as claimed in claim 4, wherein either hydrogen chloride, hydrogen bromide, or hydrogen iodide is used as a hydrogen halide to reform the used raw material.

7. A method for producing a thin film as claimed in claim 4, wherein either hydrochloric acid or sulfuric acid is used as an inorganic acid to reform the used raw material.

8. A method for producing a thin film as claimed in claim 4, wherein maleic anhydride is used as an alkene to reform the used raw material.

9. A method for producing a thin film as claimed in claim 4, wherein 2-methyl-1,3-butadiene is used as a diene to reform the used raw material.

10. A method for producing a thin film as claimed in claim 1, wherein the unreacted organometallic compound is extracted after the used raw material is subjected to a decoloring treatment by contacting the raw material with a decoloring agent, said decoloring agent comprising any of activated carbon, silica, or activated clay.

11. A method for producing a thin film as claimed in claim 2, wherein the unreacted organometallic compound is extracted after the used raw material is subjected to a decoloring treatment by contacting the raw material with a decoloring agent, said decoloring agent comprising any of activated carbon, silica, or activated clay.

12. A method for producing a thin film as claimed in claim 3, wherein the unreacted organometallic compound is extracted after the used raw material is subjected to a decoloring treatment by contacting the raw material with a decoloring agent, said decoloring agent comprising any of activated carbon, silica, or activated clay.

13. A method for producing a thin film as claimed in claim 4, wherein the unreacted organometallic compound is extracted after the used raw material is subjected to a decoloring treatment by contacting the raw material with a decoloring agent, said decoloring agent comprising any of activated carbon, silica, or activated clay.

14. A method for producing a thin as claimed in claim 5, wherein the unreacted organometallic compound is extracted after the used raw material is subjected to a decoloring treatment by contacting the raw material with a decoloring agent, said decoloring agent comprising any of activated carbon, silica, or activated clay.

15. A method for producing a thin film as claimed in claim 6, wherein the unreacted organometallic compound is extracted after the used raw material is subjected to a decoloring treatment by contacting the raw material with a decoloring agent, said decoloring agent comprising any of activated carbon, silica, or activated clay.

16. A method for producing a thin film as claimed in claim 7, wherein the unreacted organometallic compound is extracted after the used raw material is subjected to a decoloring treatment by contacting the raw material with a decoloring agent, said decoloring agent comprising any of activated carbon, silica, or activated clay.

17. A method for producing a thin film as claimed in claim 8, wherein the unreacted organometallic compound is extracted after the used raw material is subjected to a decoloring treatment by contacting the raw material with a decoloring agent, said decoloring agent comprising any of activated carbon, silica, or activated clay.

18. A method for producing a thin film as claimed in claim 9, wherein the unreacted organometallic compound is extracted after the used raw material is subjected to a decoloring treatment by contacting the raw material with a decoloring agent, said decoloring agent comprising any of activated carbon, silica, or activated clay.

19. A method for producing a thin film as claimed in claim 1, including a step of removing oxygen from the used raw material before the reforming treatment and/or the decoloring treatment.

20. A method for producing a thin film as claimed in claim 2, including a step of removing oxygen from the used raw material before the reforming treatment and/or the decoloring treatment.

21. A method for producing a thin film as claimed in claim 3, including a step of removing oxygen from the used raw material before the reforming treatment and/or the decoloring treatment.

22. A method for producing a thin film as claimed in claim 4, including a step of removing oxygen from the used raw material before the reforming treatment and/or the decoloring treatment.

23. A method for producing a thin film as claimed in claim 5, including a step of removing oxygen from the used raw material before the reforming treatment and/or the decoloring treatment.

24. A method for producing a thin film as claimed in claim 6, including a step of removing oxygen from the used raw material before the reforming treatment and/or the decoloring treatment.

25. A method for producing a thin film as claimed in claim 7, including a step of removing oxygen from the used raw material before the reforming treatment and/or the decoloring treatment.

26. A method for producing a thin film as claimed by claim 8, including a step of removing oxygen from the used raw material before the reforming treatment and/or the decoloring treatment.

27. A method for producing a thin film as claimed by claim 9, including a step of removing oxygen from the used raw material before the reforming treatment and/or the decoloring treatment.

28. A method for producing a thin film as claimed in claim 10, including a step of removing oxygen from the used raw material before the reforming treatment and/or the decoloring treatment.

29. A method for producing a thin film as claimed in claim 11, including a step of removing oxygen from the used raw material before the reforming treatment and/or the decoloring treatment.

30. A method for producing a thin film according to claim 12, including a step of removing oxygen from the used raw material before the reforming treatment and/or the decoloring treatment.

31. A method for producing a thin film according to claim 13, including a step of removing oxygen from the used raw material before the reforming treatment and/or the decoloring treatment.

32. A method for producing a thin film as claimed in claim 14, including a step of removing oxygen from the used raw material before the reforming treatment and/or the decoloring treatment.

33. A method for producing a thin film as claimed in claim 15, including a step of removing oxygen from the used raw material before the reforming treatment and/or the decoloring treatment.

34. A method for producing a thin film as claimed in claim 16, including a step of removing oxygen from the used raw material before the reforming treatment and/or the decoloring treatment.

35. A method for producing a thin film as claimed in claim 17, including a step of removing oxygen from the used raw material before the reforming treatment and/or the decoloring treatment.

36. A method for producing a thin film as claimed in claim 18, including a step of removing oxygen from the used raw material before the reforming treatment and/or the decoloring treatment.

37. A method for producing a thin film as claimed in claim 1, wherein the unreacted organometallic compound is extracted by distillation or column chromatography.

38. A method for producing a thin film as claimed in claim 2, wherein the unreacted organometallic compound is extracted by distillation or column chromatography.

39. A method for producing a thin film according to claim 3, wherein the unreacted organometallic compound is extracted by distillation or column chromatography.

40. A method for producing a thin film according to claim 4, wherein the unreacted organometallic compound is extracted by distillation or column chromatography.

41. A method for producing a thin film according to claim 5, wherein the unreacted organometallic compound is extracted by distillation or column chromatography.

42. A method for producing a thin film according to claim 6, wherein the unreacted organometallic compound is extracted by distillation or column chromatography.

43. A method for producing a thin film according to claim 7, wherein the unreacted organometallic compound is extracted by distillation or column chromatography.

44. A method for producing a thin film according to claim 8, wherein the unreacted organometallic compound is extracted by distillation or column chromatography.

45. A method for producing a thin film as claimed in claim 9, wherein the unreacted organometallic compound is extracted by distillation or column chromatography.

46. A method for producing a thin film as claimed in claim 10, wherein the unreacted organometallic compound is extracted by distillation or column chromatography.

47. A method for producing a thin film as claimed in claim 11 wherein the unreacted organometallic compound is extracted by distillation or column chromatography.

48. A method for producing a thin film as claimed in claim 12, wherein the unreacted organometallic compound is extracted by distillation or column chromatography.

49. A method for producing a thin film as claimed in claim 13, wherein the unreacted organometallic compound is extracted by distillation or column chromatography.

50. A method for producing a thin film as claimed in claim 14, wherein the unreacted organometallic compound is extracted by distillation or column chromatography.

51. A method for producing a thin film as claimed in claim 15, wherein the unreacted organometallic compound is extracted by distillation or column chromatography.

52. A method for producing a thin film as claimed in claim 16, wherein the unreacted organometallic compound is extracted by distillation or column chromatography.

53. A method for producing a thin film as claimed in claim 17, wherein the unreacted organometallic compound is extracted by distillation or column chromatography.

54. A method for producing a thin film as claimed in claim 18, wherein the unreacted organometallic compound is extracted by distillation or column chromatography.

55. A method for producing a thin film as claimed in claim 19, wherein the unreacted organometallic compound is extracted by distillation or column chromatography.

56. A method for producing a thin film as claimed in claim 20, wherein the unreacted organometallic compound is extracted by distillation or column chromatography.

57. A method for producing a thin film as claimed in claim 21, wherein the unreacted organometallic compound is extracted by distillation or column chromatography.

58. A method for producing a thin film as claimed in claim 22, wherein the unreacted organometallic compound is extracted by distillation or column chromatography.

59. A method for producing a thin film as claimed in claim 23, wherein the unreacted organometallic compound is extracted by distillation or column chromatography.

60. A method for producing a thin film as claimed in claim 24, wherein the unreacted organometallic compound is extracted by distillation or column chromatography.

61. A method for producing a thin film as claimed in claim 25, wherein the unreacted organometallic compound is extracted by distillation or column chromatography.

62. A method for producing a thin film as claimed in claim 26, wherein the unreacted organometallic compound is extracted by distillation or column chromatography.

63. A method for producing a thin film as claimed in claim 27, wherein the unreacted organometallic compound is extracted by distillation or column chromatography.

64. A method for producing a thin film as claimed in claim 28, wherein the unreacted organometallic compound is extracted by distillation or column chromatography.

65. A method for producing a thin film as claimed in claim 11, wherein the unreacted organometallic compound is extracted by distillation or column chromatography, including a step of removing oxygen from the used raw material before the reforming treatment and/or the decoloring treatment.

66. A method for producing a thin film as claimed in claim 12, wherein the unreacted organometallic compound is extracted by distillation or column chromatography, including a step of removing oxygen from the used raw material before the reforming treatment and/or the decoloring treatment.

67. A method for producing a thin film as claimed in claim 13, wherein the unreacted organometallic compound is extracted by distillation or column chromatography.

68. A method for producing a thin film as claimed in claim 14, wherein the unreacted organometallic compound is extracted by distillation or column chromatography.

69. A method for producing a thin film as claimed in claim 15, wherein the unreacted organometallic compound is extracted by distillation or column chromatography.

70. A method for producing a thin film as claimed in claim 16, wherein the unreacted organometallic compound is extracted by distillation or column chromatography.

71. A method for producing a thin film as claimed in claim 17, wherein the unreacted organometallic compound is extracted by distillation or column chromatography.

72. A method for producing a thin film as claimed in claim 18, wherein the unreacted organometallic compound is extracted by distillation or column chromatography.

* * * * *